United States Patent [19]
Shoberg et al.

[11] Patent Number: 5,957,970
[45] Date of Patent: Sep. 28, 1999

[54] METHOD OF FABRICATING A MEDICAL ELECTRICAL LEAD

[75] Inventors: Bret R. Shoberg, Corcoran; Matthew D. Bonner, Plymouth; Timothy G. Laske, Shoreview, all of Minn.

[73] Assignee: Medtronic, Inc., Minneapolis, Minn.

[21] Appl. No.: 09/025,485

[22] Filed: Feb. 18, 1998

[51] Int. Cl.⁶ ................................................ A61N 1/05
[52] U.S. Cl. ........................................................ 607/722
[58] Field of Search .................................. 607/119, 122, 607/116, 123, 125; 29/825, 746

[56] References Cited

U.S. PATENT DOCUMENTS

| | | |
|---|---|---|
| 4,161,952 | 7/1979 | Kinney et al. . |
| 4,934,049 | 6/1990 | Kiekhafer et al. . |
| 5,016,646 | 5/1991 | Gotthardt et al. .................. 607/122 |
| 5,115,818 | 5/1992 | Holleman et al. .................. 607/122 |
| 5,584,873 | 12/1996 | Shoberg et al. .................... 607/122 |
| 5,676,694 | 10/1997 | Boser et al. . |

*Primary Examiner*—William E. Kamm
*Assistant Examiner*—George R. Evanisko
*Attorney, Agent, or Firm*—Reed A. Duthler; Harold R. Patton

[57] ABSTRACT

A method of producing a lead which is isodiametric or nearly so over the region in which an elongated coiled electrode is located and which can optionally be manufactured starting from a single extruded tubular lead body of constant diameter and the lead so produced. Rather than molding the electrode into the surface of the lead or machining the electrode so that it is flush with the surface of the lead, the present invention instead employs an extruded, multiple lumen lead body of circular cross-section which has material cut away or otherwise removed in one or more regions spaced from one another around the lead body and extending longitudinally along the region of the lead body where the coil electrode is to be located or a lead body which is so molded. The areas in which material is removed or is absent are preferably located in regions where the lead body wall is thickest, for example between adjacent lumens. The removal of material may result in one or more elongated, generally planar surfaces spaced from one another around the circumference of the lead body or may result in elongated indentations spaced from one another around the circumference of the lead body. The removal or absence of material renders the lead body more compressible in the region the electrode is to be located.

12 Claims, 3 Drawing Sheets

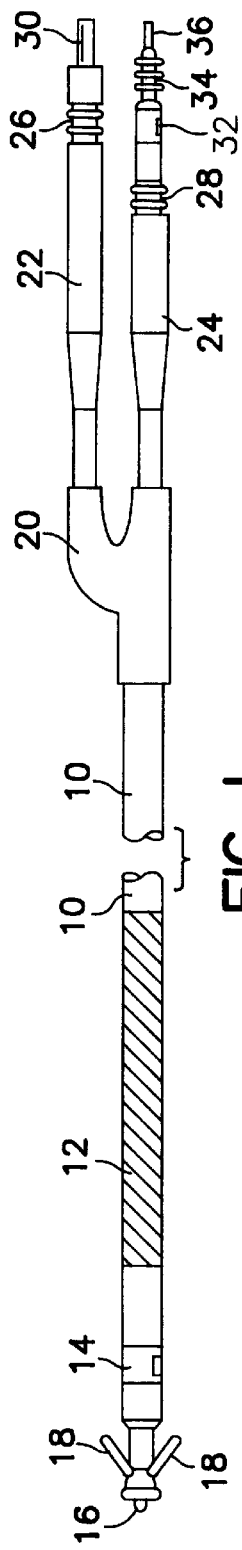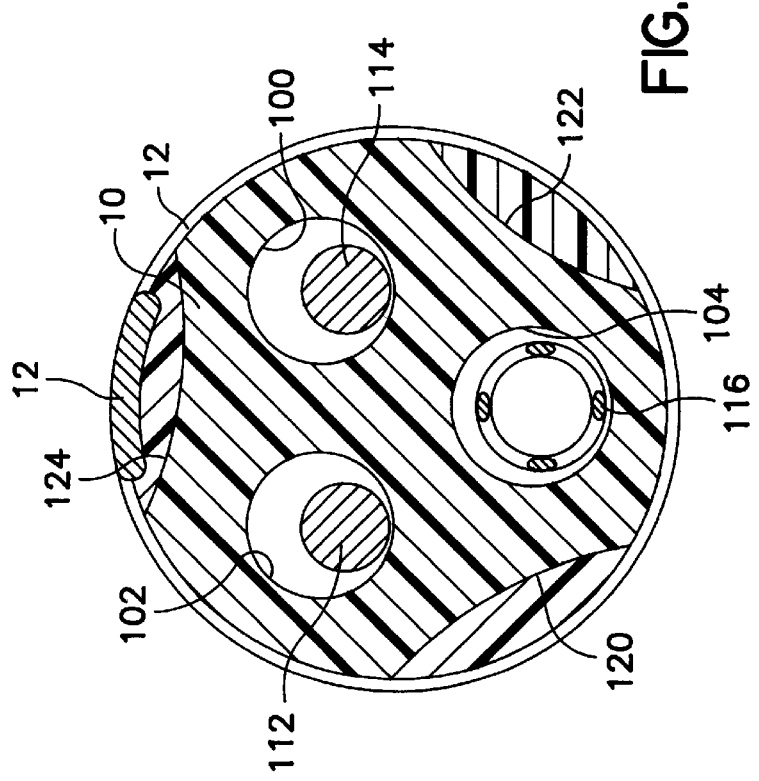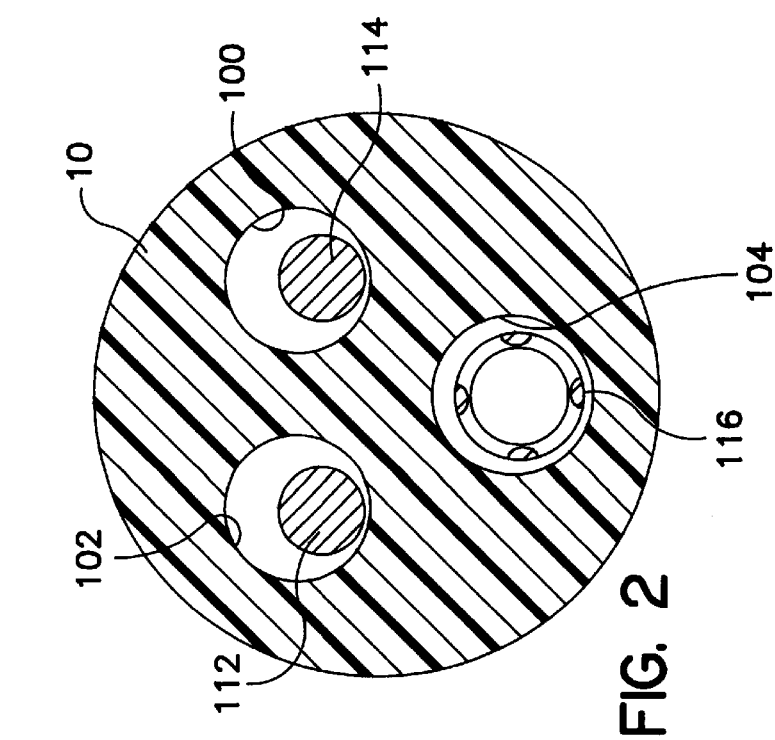

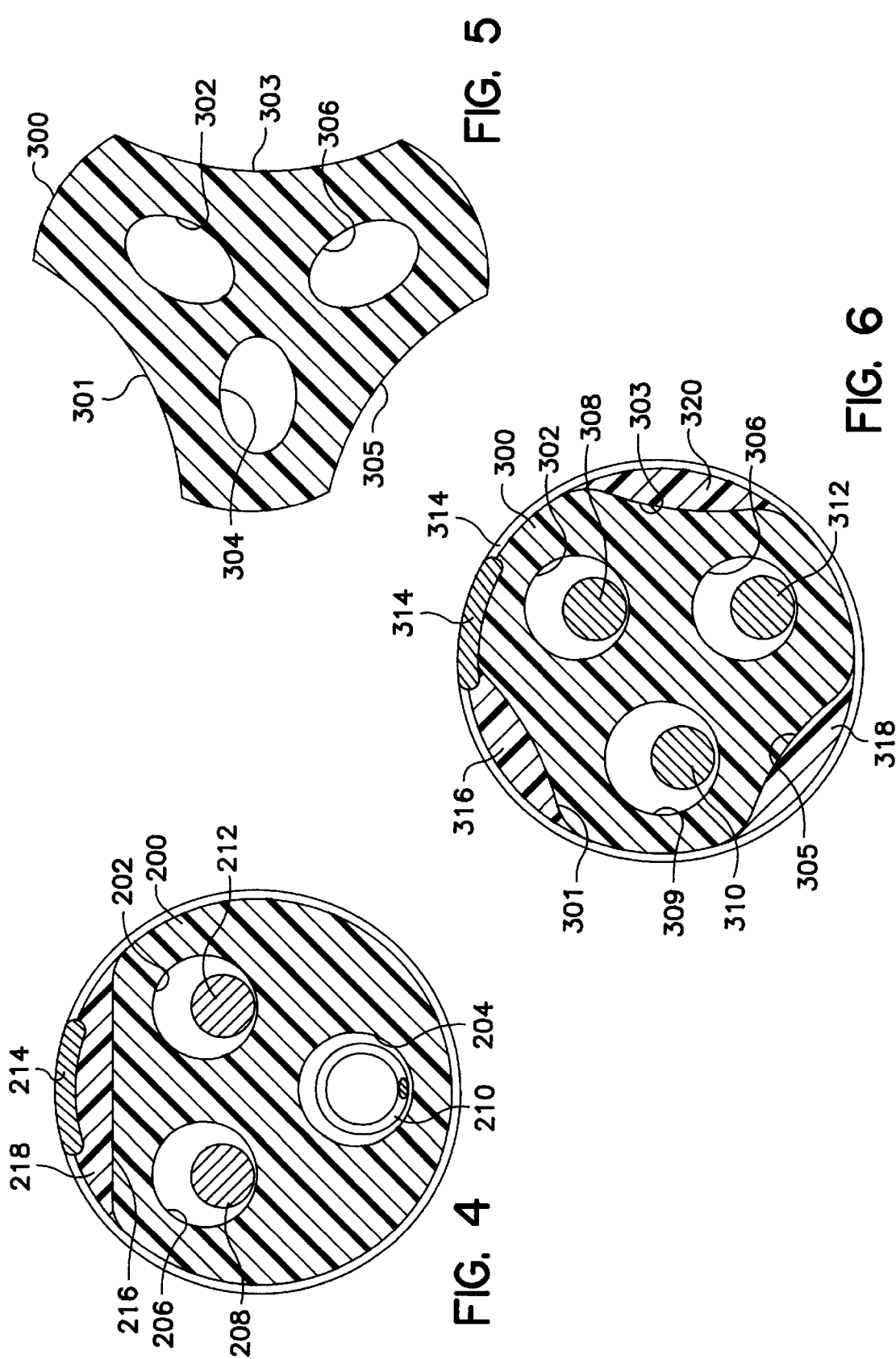

METHOD OF FABRICATING A MEDICAL ELECTRICAL LEAD

BACKGROUND OF THE INVENTION

The present invention relates to implantable medical electrical leads, and more particularly relates to implantable cardioversion/defibrillation leads.

Transvenous cardioversion and defibrillation leads typically employ cardioversion or defibrillation electrodes taking the form of elongated metal coils. These coils may be applied to the exterior surface of the lead body, as disclosed in U.S. Pat. No. 4,934,049 issued to Kiekhafer et al. and optionally thereafter backfilled. Alternatively, the electrode coils may be molded into the electrode body to provide a flush surface or the coils may be machined to provide a flush surface as in U.S. Pat. No. 4,161,952, issued to Kinney et al. The latter approaches provide leads with a uniform outer diameter at the cost of a more complex manufacturing technique. Leads employing coils which are mounted around a lead body having a circular cross-section are substantially easier to manufacture, however, they do provide an increase in lead diameter over the region in which the electrode is located. This in turn requires an increase in the required inner diameter of the introducer used with the lead.

SUMMARY OF THE INVENTION

The present invention is directed toward producing a lead which is isodiametric or nearly so over the region in which an elongated coiled electrode is located and which can be manufactured starting from a single extruded tubular lead body of constant diameter. Rather than molding the electrode into the surface of the lead or machining the electrode so that it is flush with the surface of the lead, the present invention instead employs an extruded, multiple lumen lead body of circular cross-section which has material cut away or otherwise removed in one or more regions spaced from one another around the lead body and extending longitudinally along the region of the lead body where the coil electrode is to be located.

The areas in which material is removed are preferably located in regions where the lead body wall is thickest, for example between adjacent lumens. The removal of material may result in one or more elongated, generally planar surfaces spaced from one another around the circumference of the lead body or may result in elongated indentations spaced from one another around the circumference of the lead body. The removal of material renders the lead body more compressible in the region the electrode is to be located.

The electrode may take the form of a coil which is sized to display an outer diameter approximately equal to the outer diameter of the unmodified lead body. The lead body is inserted into the electrode coil, for example, by extending the lead body in order to reduce its diameter, and the electrode coil exerts a compressive force against the lead body. Because portions of the lead body have been cut away, the lead body is more easily deformed by the coiled electrode and does not tend to expand significantly beyond its original diameter. After insertion of the lead body into the electrode, voids or spaces between the lead body and the coiled electrode may be backfilled using conventional backfilling processes if desired or the compressive force applied to the lead body by the coiled conductor may be employed to retain the coils in position on the lead body.

BRIEF DESCRIPTION OF THE DRAWINGS

FIG. 1 is a plan view of an implantable lead of the type in which the present invention may be practiced.

FIG. 2 is cross-sectional view through the lead of FIG. 1 proximal to the cardioversion/defibrillation electrode.

FIG. 3 is cross-sectional view through the lead of FIG. 1 in the region of the cardioversion/defibrillation electrode.

FIG. 4 is a cross-sectional through a first alternative embodiment of a lead according to the present invention.

FIG. 5 is a cross-sectional view through a embodiment of a lead body for use in a second alternative embodiment of a lead according to the present invention.

FIG. 6 is a cross-sectional view through a second alternative embodiment of a lead according to the present invention incorporating the lead body of FIG. 5.

DETAILED DESCRIPTION OF THE PREFERRED EMBODIMENTS

Figure 8:
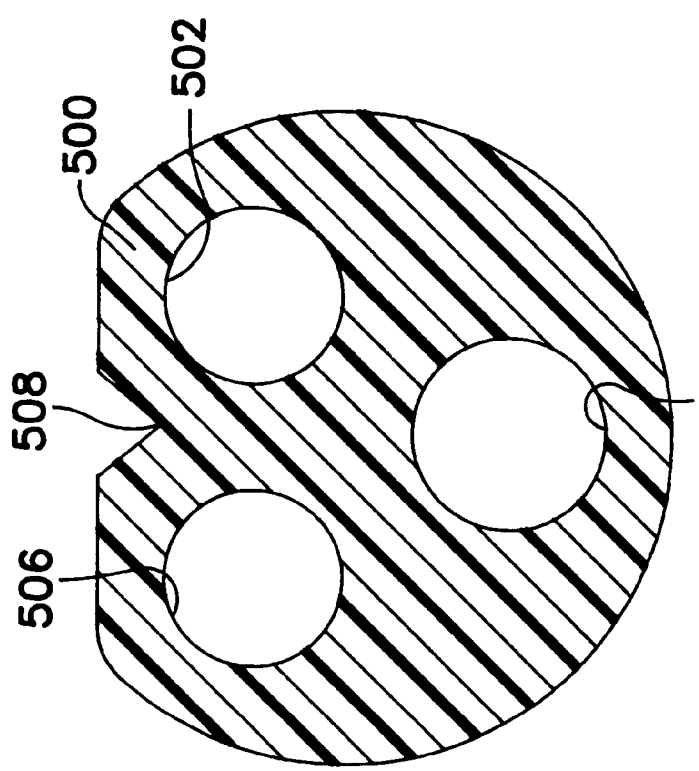
FIG. 8 is a cross-sectional view through a embodiment of a lead body for use in a fourth alternative embodiment of a lead according to the present invention.

FIG. 1 is a plan view of a defibrillation lead of the type in which the present invention may usefully be practiced. The present invention, of course, may also be usefully practiced in the context of other medical electrical leads, such as cardiac pacing leads, nerve and muscle stimulation leads, and so forth.

The lead of FIG. 1 is provided with an elongated insulative lead body 10, preferably fabricated of silicone rubber, polyurethane or other biocompatible, compressible elastomer. At the proximal end of the lead, it carries an elongated defibrillation 12, a ring electrode 14 and a tip electrode 16, each coupled to a conductor located within the lead body 10. Tines 18 are provided in maintaining electrode 16 in contact with the tissue of the right ventricle. Electrodes 16, 14 and 12 may correspond to any conventionally available pacing and defibrillation electrodes.

The proximal end of the lead carries a connector assembly, beginning with a molded lead bifurcation sleeve 20, which splits off two of the conductors within lead body 10 to a bipolar, in-line connector assembly 24, generally corresponding to the IS-1 connector standard for pacing leads. Connector assembly 24 is provided with a first set of sealing rings 28, a connector ring 32, a second sealing rings 34 and connector pin 36. Connector pin 36 is coupled to the conductor which extends through the lead body 10 to tip electrode 16. Connector ring is coupled to the conductor which extends through the lead body 10 to ring electrode 14. The conductor coupled to defibrillation electrode 12 extends into connector assembly 22, which carries a set of sealing rings 26 and a connector pin 36, coupled to the conductor extending through lead body 10 to defibrillation electrode 12. The illustrated connector assemblies are conventional elements, and may correspond to any of the numerous known electrical connector assemblies provided on implantable medical leads.

Although not visible in FIG. 1, it should be noted that the elongated conductors passing through lead body 10 may be any of the various known available conductors for use in conjunction with implantable electrical leads, including monofilar or multifilar coiled conductors, bundled stranded conductors, and the like. In the specific context of the lead illustrated in FIG. 1, the connector coupling connector pin 32 to electrode 16 takes the form of a multifilar coiled conductor to allow passage of a stylet therethrough, while the conductors coupling ring electrode 14 to connector ring 32 and coupling defibrillation electrode coil 12 to connector pin 30 take the form of bundled, stranded wires, provided with a coating of PTFE. However, the present invention is believed workable in the context of any of the numerous conductors known for use in implantable electrical leads, in any combination with one another.

FIG. 2 illustrates a cross-section through lead body 10, illustrating the configuration of lead body 10 as extruded. Lead body 10 includes three conductor lumens 100, 102 and 104. In this view it can be seen that the conductor lumens contain three conductors, comprising conductors 112 and 114 which take the form of PTFE coated bundled stranded wires having a generally straight configuration and a more conventional multifilar coiled conductor 116. Conductors 112 and 114 in particular may take the form of bundled stranded wires fabricated of silver cored MP35N wire, including 49 filars, coated with an extruded coating of PTFE. Conductor coil 16 may take the form of a multifilar coil of four MP35N wires having an internal lumen in order to allow passage of a stylet therethrough. One of conductors 112 and 114 is coupled to electrode coil 12, for example using cross groove crimp sleeves as disclosed in U.S. Pat. No. 5,676,694, issued to Boser et al., incorporated herein by reference in its entirety. However, any mechanism for interconnecting the conductor and the electrode coil, such crimping, swaging or welding may also be used.

FIG. 3 is a cross-sectional view of the lead of FIG. 1, taken through coil electrode 12. In this view, electrode coil 12, which has an outer diameter close to that of the lead body 10 proximal thereto the is visible in cross-section, and a portion of one of its turns edge extending beyond compressed lead body 10 is also visible. Lead body 10, prior to insertion into electrode coil 12 has been trimmed by removing three sections of the lead body, trimming it to assume a generally rounded triangular form in cross-section or alternatively was molded to assume this cross section. The three trimmed surfaces of lead body 10 take the form of circumferentially spaced, elongated planar surfaces extend the length of electrode 12 and are illustrated at 120, 122 and 124. The lead body, after trimming, is stretched slightly and inserted into electrode coil 12, and thereafter allowed to expand to the extent allowed by electrode coil 12, expanding somewhat to fill the spaces in between individual turns of electrode coil 12. Thereafter, the lead may optionally be backfilled with silicone rubber adhesive according to the procedure described in U.S. Pat. No. 4,934,049 issued to Kiekhafer et al., or otherwise, to provide adhesive backfills in regions 126, 128 and 130, returning the external configuration of the lead body to a general round configuration. All other labeled components in the drawing correspond to identically labeled components in FIG. 2.

FIG. 4 is a cross-section of an alternative embodiment of the lead according to the present invention. In this case, lead body 2 is trimmed along only one side, to provide a single elongated, generally planar trimmed surface 216 or was molded to provide the illustrated cross section. The lead otherwise corresponds to that issued in FIG. 3 and includes three lumens, 202, 204 and 206 carrying conductors 208, 210 and 212. The electrode coil 214 is visible in cross-section and a portion of one of its turns is visible where it exceeds the diameter of lead body 200. Backfill 218 is provided in the same fashion as described above in conjunction with FIG. 3. This particular embodiment is believed useful in embodiments in which coiled conductor 210 is employed to rotate a fixation helix. By limiting the cut out or cutaway portion to the side of the lead opposite lumen 204, distortion of configuration of lumen 204 is limited, minimizing the chance that deformation of the lumen will interfere with the ability to rotate conductor 210.

FIG. 5 is a cross-section of a third embodiment of a lead according to the present invention in which trimmed away areas 301, 303 and 305 are provided in lead body 300. Trimmed areas 301,303 and 305 take the form of elongated indentations extending longitudinally along the intended length the electrode coil to be applied thereafter. In this embodiment of the invention, the lumens 302, 304 and 306 are generally egg shaped, with the desired result that upon compression they will assume a more rounded or circular cross-sectional configuration.

FIG. 6 is a cross-sectional view through a lead employing lead body 300. In this view it can be seen that after compression by electrode coil 314, the lumens 302, 304 and 306 of lead body 310 assume a more circular configuration. Backfills 316, 318 and 320 correspond to the backfilled areas in FIGS. 3 and 4. Conductors 308, 310 and 312 are also illustrated.

Figure 7:
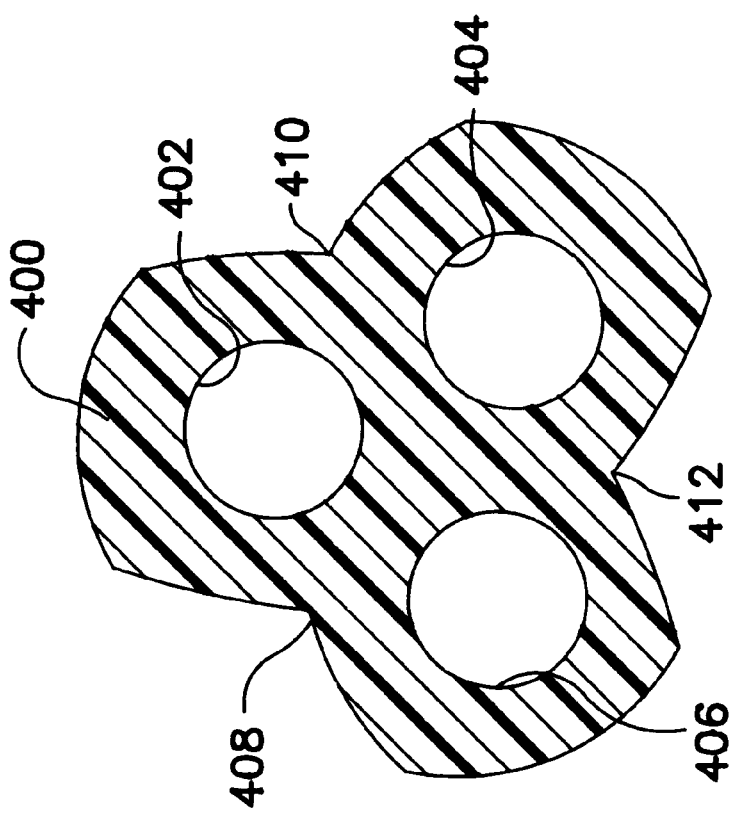
FIG. 7 is a cross-sectional view through a embodiment of a lead body for use in a third alternative embodiment of a lead according to the present invention.

FIG. 7 is a cross-sectional view through a third embodiment of a lead body appropriate for use in conjunction with the present invention. In this case, the lead body 400 is provided with three generally circular lumens 402, 404 and 406, and material is removed from the previously round lead body to define elongated indentations 408, 410 and 412.

FIG. 8 is a cross-section through a fourth alternative embodiment of a lead body according to the present invention in which material is removed from lead body to define only a single elongated indentation 508, located between lumens 502 and 506. This embodiment like that illustrated in FIG. 4 is believed particularly desirable in embodiments in which a rotatable coiled conductor is to be inserted in lumen 504.

In conjunction with the above disclosure, we claim:

1. A method of fabricating a medical electrical lead, comprising:

selecting an elongated lead body having a circular cross section, having at least one internal longitudinally extending lumen and fabricated of a compressible, biocompatible plastic;

removing said plastic along at least one longitudinally extending region of said lead body to define a non-circular cross section;

mounting an elongated electrode coil around said lead body to compress said lead body along said longitudinally extending region; and locating an elongated conductor within said lead body and coupled to said electrode coil.

2. A method according to claim 1 wherein said selecting step comprises selecting a lead body having a lead body wall surrounding said at least one longitudinally extending lumen and wherein said removing step comprises removing material along at least one longitudinally extending region located in an area having relatively greater wall thickness than other portions of said wall prior to said removal of said plastic.

3. A method according to claim 1 or claim 2 wherein said mounting step comprises mounting an electrode coil wherein said electrode coil has an outer coil diameter approximately equal to that of said circular cross section of said lead body.

4. A method according to claim 1 or claim 2 further comprising backfilling plastic in said at least one longitudinally extending region after said mounting step.

5. A method according to claim 1 or claim 2 wherein said selecting step comprises selecting a lead body wherein said at least one lumen has a generally ovoid cross section.

6. A method according to claim 1 or claim 2 wherein said removing step comprises removing said plastic along multiple, circumferentially spaced, longitudinally extending regions of said lead body to define a non-circular cross section.

7. A method of fabricating a medical electrical lead, comprising:

selecting an elongated lead body having a circular cross section, having at least one internal longitudinally extending lumen and fabricated of a compressible, biocompatible plastic and having a longitudinally extending indentation relative to said circular cross section along at least one longitudinally extending region to define a non-circular cross section;

mounting an elongated electrode coil around said lead body to compress said lead body along said longitudinally extending region; and locating an elongated conductor within said lead body and coupled to said electrode coil.

8. A method according to claim 7 wherein said selecting step comprises selecting a lead body having a lead body wall surrounding said at least one longitudinally extending lumen and having a portion of said lead body wall proximal to and extending longitudinally from said indentation with relatively greater wall thickness than other portions of said wall proximal to but circumferentially spaced from said indentation.

9. A method according to claim 7 or claim 8 wherein said mounting step comprises mounting an electrode coil wherein said electrode coil has an outer coil diameter approximately equal to that of said circular cross section of said lead body.

10. A method according to claim 7 or claim 8 further comprising backfilling plastic in said at least one longitudinally extending indentation after said mounting step.

11. A method according to claim 7 or claim 8 wherein said selecting step comprises selecting a lead body wherein said at least one lumen has a generally ovoid cross section.

12. A method according to claim 7 or claim 8 wherein said selecting step comprises selecting a lead body having multiple, circumferentially spaced, longitudinally extending indentations to define a non-circular cross section.

* * * * *